US00PP12999P2

(12) United States Plant Patent
Olesen et al.

(10) Patent No.: US PP12,999 P2
(45) Date of Patent: Sep. 24, 2002

(54) HYBRID TEA ROSE PLANT NAMED 'POULDRA'

(76) Inventors: L Pernille Olesen, Hillerødvejen 49, DK-3480 Fredensborg (DK); Mogens N. Olesen, Hillerødvejen 49, DK-3480 Fredensborg (DK)

( * ) Notice: Subject to any disclaimer, the term of this patent is extended or adjusted under 35 U.S.C. 154(b) by 0 days.

(21) Appl. No.: 09/270,178

(22) Filed: Mar. 15, 1999

(51) Int. Cl.[7] ..... A01H 5/00
(52) U.S. Cl. ..... Plt./102
(58) Field of Search ..... Plt./130, 138, 141, Plt./149, 102, 107

(56) References Cited

PUBLICATIONS

Community Plant Variety Office "Certificate on the Grant ... " 7 pages. Aug. 3, 1998. EU.

Research Centre for Cultivar Testing "Decision" 1 page Feb. 22, 1999. Poland.

Canadian Food Inspection Agency "Applications Accepted for Filling" 1 page. Apr. 1999.

UPOV–ROM, 2001/01, Plant Variety Database, GTI Jouve Retrieval Software, citation for 'POULdra'.*

UPOV–ROM, 2000/04, Plant Variety Database, GTI Jouve Retrieval Software, 2 citations for 'POULdra'.*

* cited by examiner

*Primary Examiner*—Howard J. Locker

(57) ABSTRACT

A new garden rose plant which has abundant, deep pink flowers and attractive foliage. This new and distinct variety has shown to be uniform and stable in the resulting generations from asexual propagation.

2 Drawing Sheets

SUMMARY OF THE INVENTION

The present invention constitutes a new and distinct variety of garden rose plant which originated from a controlled crossing between 'Margaret Merril' and unnamed seedling. The two parents were crossed and the resultng seeds were planted in a controlled environment. The new variety is named 'POULdra'.

The new rose may be distinguished from its seed parent, 'Margaret Merril', by the following combination of characteristics:

1. The seed parent has pure white flowers and 'POULdra' has deep pink flowers;
2. The seed parent has a larger flower size;
3. The seed parent has a higher number of flower petals when compared to 'POULdra'.

The new variety may be distinguished from its pollen parent, an unnamed seedling created by the same inventors, by the following combination of characteristics:

1. The pollen parent has no fragrance while 'POULdra' is exceptionally fragrant;
2. The pollen parent dose not grow as tall as 'POULdra';
3. The pollen parent has more petals (very double) while 'POULdra' flowers are double.

The objective of the hybridization of this rose variety for nursery and garden use was to create a new and distinct variety with unique qualities, such as:

1. Uniform and abundant flowers;
2. Vigorous, compact growth;
3. Exceptional fragrance;
4. Disease Resistance.

This combination of qualities is not present in previously available commercial cultivars of this type and distinguish 'POULdra' from all other varieties of which we are aware.

As part of their rose development program, L. Pernille Olesen and Mogens N. Olesen germinated the seeds from the aforementioned hybridization and conducted elaluations on the resulting seedlings in a controlled environment in Fredensborg, Denmark.

'POULdra' was selected in the summer of 1988 by the inventors as a single plant from the aforementioned hybridization.

Asexual reproduction of 'POULdra' by traditional budding was first done by L. Pernille and Mogens N. Olesen in August 1989, at their nursery in Fredensborg, Denmark. This initial and other subsequent propagations conducted in controlled environments have demonstrated that the characteristics of 'POULdra' are true to type and are transmitted from one generation to the next.

BRIEF DESCRIPTION OF THE DRAWING

The accompanying color illustrations shows as true as is reasonably possible to obtain in color photographs of this type, the typical characteristics of the buds, flowers, leaves, and stems of 'POULdra'. Specifically illustrated in SHEET 1:

1. Stem of plant showing branching and the attachment of leaves, buds, and peduncles;

2. Flower bud, partially opened bud, and open bloom;

3. Flower petals, detached.

Specifically illustrated in SHEET 2:

4. Speals and pedicel;

5. Flowering stem as well as a bare stem exhibiting thorns;

6. Leaves.

DETAILED DESCRIPTION OF THE VARIETY

The following is a description of 'POULdra', as observed in its outdoor growth in a field nursery in Jackson County, Oreg. Observations were conducted during August, 1998. Color references are made using The Royal Horticultural Society (London, England) Colour Chart, 1995, except where common terms of color are used.

For a comparison, several physical characteristics of the rose variety 'POULari', a Hybrid Tea rose variety, from the same inventors, described and illustrated in U.S. Plant Pat. No. 9,274 and issued on Sep. 5, 1995 is compared to 'POULdra' in Chart 1.

CHART 1

| | 'POULdra' | 'POULari' |
|---|---|---|
| Upper Petal Surface of open Flower | Red Purple Group 57B–57C | White Group 157D |
| Petalage | Double, with 20–30 petals | Very Double, with 55–70 petals |
| Color of upper leaf surface of mature foliage | Green Group 137A–147A | Green Group 147A |

Parents:
- *Seed parent.*—'Margaret Merril'.
- *Pollen parent.*—Unnamed seedling.

Classification:
- *Botanical.*—*Rosa hybrida.*
- *Commercial.*—Shrub.

FLOWER AND FLOWER BUD

Blooming habit: Continuous.

Flower bud:
- *Size.*—Upon opening, 35 mm–40 mm in length from base of receptacle to end of bud.
- *Bud form.*—Long and high-centered.
- *Bud color.*—Red-Purple Group 66C–67A at ¼ opening.
- *Sepals.*—Green Group 137A. Strong foliaceous appendages on three of the five sepals. Sepal tips extend well past tip of bud, and exhibit serrated margins. Surfaces of sepals are slightly pubescent. Stipitate glands are present on margins and the outer surface of sepals.
- *Receptacle.*—Surface: Generally smooth. Shape: Broadly funnel shaped. Size: Medium, 5 mm (h)×8 mm (w). Color: Green Group 143C with some intonations of Greyed-Red Group 179A.
- *Peduncle.*—Surface: Exhibits stipitate glands and prickles. Length: 60–70 mm average length. Color: Green Group 143C with strong intonations of Greyed-Red Group 179A. Strength: Upright.
- *Borne.*—Varies from 1 to 4 buds per flowering stem.

Flower bloom:
- *Fragrance.*—Strong, spicy scent.
- *Duraction.*—As a cut flower 5 to 6 days. The blooms have a duration on the plant of approximately 5 to 7 days. Petals fall cleanly away from plant.
- *Size.*—Medium. Average flower diameter is 100 mm when open.
- *Form.*—Shallow-cup.
- *Shape of flower when viewed from the side.*—Upon opening, upper part: Convex. Upon opening, lower part: Convex. Open flower, upper part: Flattened convex. Open flower, lower part: Flat.
- *Petalage.*—Double. Average range 20–30 petals under normal conditions with 0–5 petaloids.

Color:
- *Upon opening, petals.*—Outermost petals: Upper Surface: Red-Purple Group 66A–66B. Reverse Side: Red-Purple Group 66A–66B. Innermost petals: Upper Surface: Red-Purple Group 57A–66A. Reverse Side: Red-Purple Group 57A–66A.
- *Upon opening, basal petal spots.*—Outermost petals: Outer Side: Green-Yellow Group 1B. Inner Side: Yellow Group 13B. Innermost petals: Outer Side: Green-Yellow Group 1B. Inner Side: Yellow Group 13B.
- *After opening, petals.*—Outermost petals: Upper Surface: Red-Purple Group 57B–57C,. Reverse Side: Red-Purlpe Group 57B–57C. Innermost petals: Upper Surface: Red-Purple Group 57B–57C. Reverse Side: Red-Purple Group 57B–57C.
- *After opening, basal petal spots.*—Outermost petals: Outer Side: Yellow Group 4B. Inner Side: Yellow Group 4B. Innermost petals: Outer Side: Yellow Group 4A. Inner Side: Yellow Group 4A.

General tonality: On open flower Red-Purple Group 57B. No change in the general tonality at the end of the 3rd day. Afterwards, general tonality is Red-Purple Group 57C–57D.

Petals:
- *Petal reflex.*—Petals slightly reflexed except the outermost petals which are reflexed.
- *Petal edge.*—Entire.
- *Shape.*—Round to deltoid shaped.
- *Petaloids.*—Present. Quantity: 0–5.
- *Thickness.*—Thick.
- *Arrangement.*—Informal.

Reproductive organs:
- *Pollen.*—Color: Greyed-Orange Group 163B. Abundance: Average.
- *Anthers.*—Size: Medium. Color: Immature: Yellow-Orange Group 14C with intonation in the center of Orange Group 25C. Mature: Brown Group 200B. Abundance: Abundant.
- *Filaments.*—Color: At point of anther attachment Yellow Group 13C with Green tones. The upper portion of the filament is Red-Purple Group 57B which fades as flower matures.
- *Stigmas.*—Location: Stigmas and Anthers generally positioned at same level. Color: Yellow-Green Group 145D.
- *Styles.*—Color: Green-White Group 157C with intonations of Red-Purple Group 57B below stigmas. Other: Styles have fine hairs.
- *Hips.*—None observed.

PLANT

Plant growth: Moderate, upright to bushy, when grown as a budded, field grown plant on *Rosa multiflora* understock. The average height of the plant is 100 cm and the average width is 70 cm.

Stems:
- *Color.*—Young wood: Yellow-Green Group 144B. Older wood: Yellow-Green Group 144A.
- *Thorns.*—Incidence: Moderate. Size: Average length: 7 mm–8 mm. Color: Yellow-Green Group 145B–145C. with intonation of Greyed-Red Group 179A at the base of thorn. Shape: Linear, with downward hook.

*Surface.*—Young wood: Smooth. Older wood: Smooth.

*Length.*—80 to 90 cm.

Plant foliage: Typical number of leaflets on leaves in the middle of the stem: 5 leaflets.

*Leaf size.*—Medium, 140 mm (L)×110–120 mm (w).

*Abundance.*—Average.

*Color.*—Upper Leaf Surface: Green Group 137A–147A. Lower Leaf Surface: Green Group 138B. Juvenile foliage: Upper Surface: Green Group 137C–144A. Lower surface is Green Group 138A. Anthocyanin intonation: Location: Strong anthocyanin intonation on juvenile leaves, rachis, petiole, peduncles, sepals, and stems. Color: Greyed-Red Group 181A.

Plant leaves and leaflets:

*Stipules.*—Size: 16 mm–18 mm. Color: Green Group 137B. Presence of stipitate glands: On margins of stipules.

*Petiole.*—Length: 30 mm–40 mm. Color: Green Group 137B. Underneath: Small prickles present. Margins: Fine hairs and stipitate glands observed. Upper surface: Limited numbers of fine hairs.

*Rachis.*—Color: Green Group 137B. Underneath: Small prickles present. Margins: No hairs observed.

*Leaflet.*—Edge: Serrated. Shape: Ovate to round. Other: Glossy and thick.

Disease resistance: Above average resistance to black spot, and Botrytis under normal growing conditions in Jackson County, Oreg.

Cold hardiness: 'POULdra' has been found to be resistant to damage from cold, heat and drought damage in USDA Zone 7.

We claim:

1. A new and distinct variety of rose plant of the shrub class, substantially as herein illustrated and described as a distinct and novel rose variety due to its abundant, dark pink flowers, strong fragrance, disease resistance, and extended period of bloom.

* * * * *

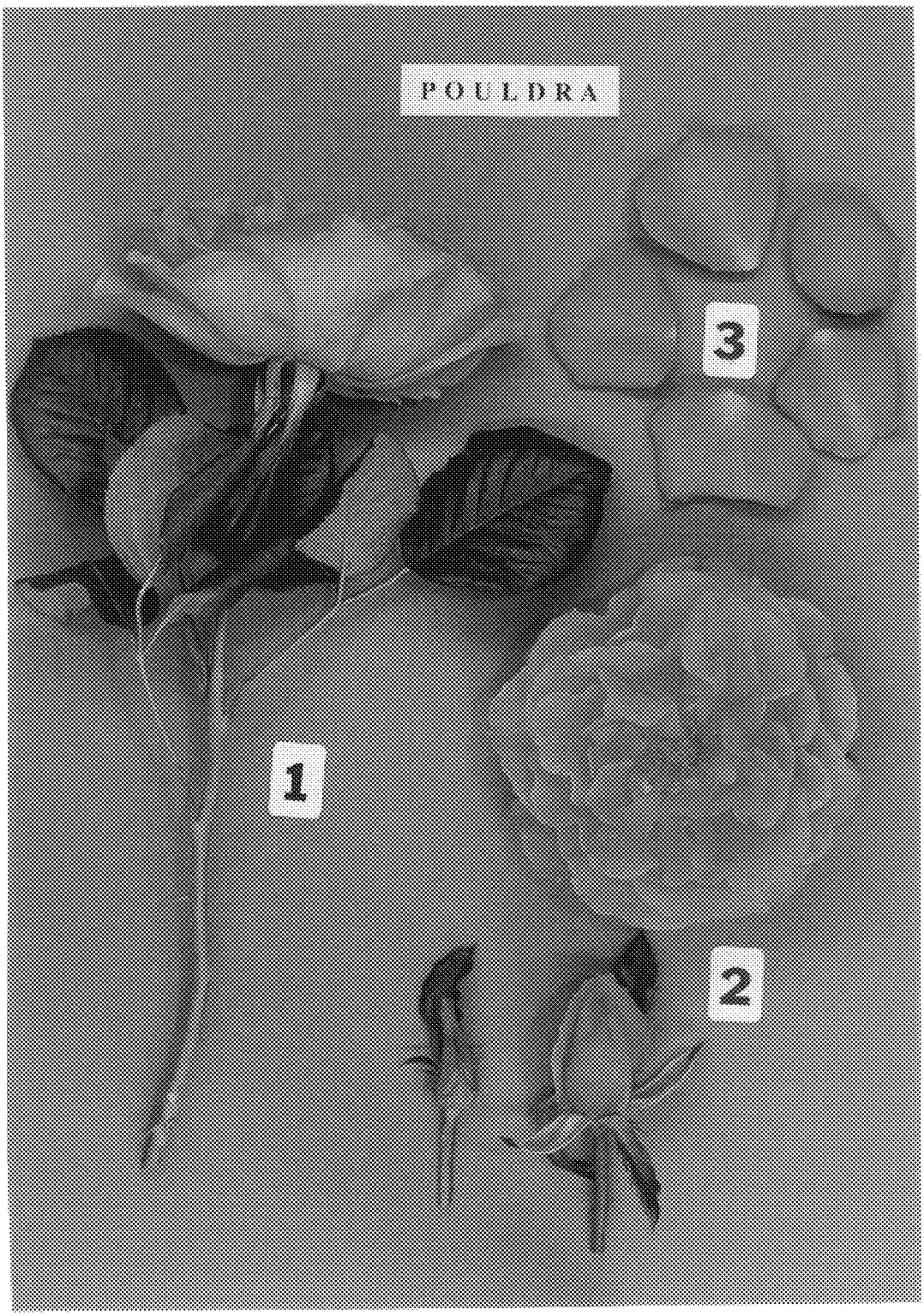
POULDRA
3
1
2

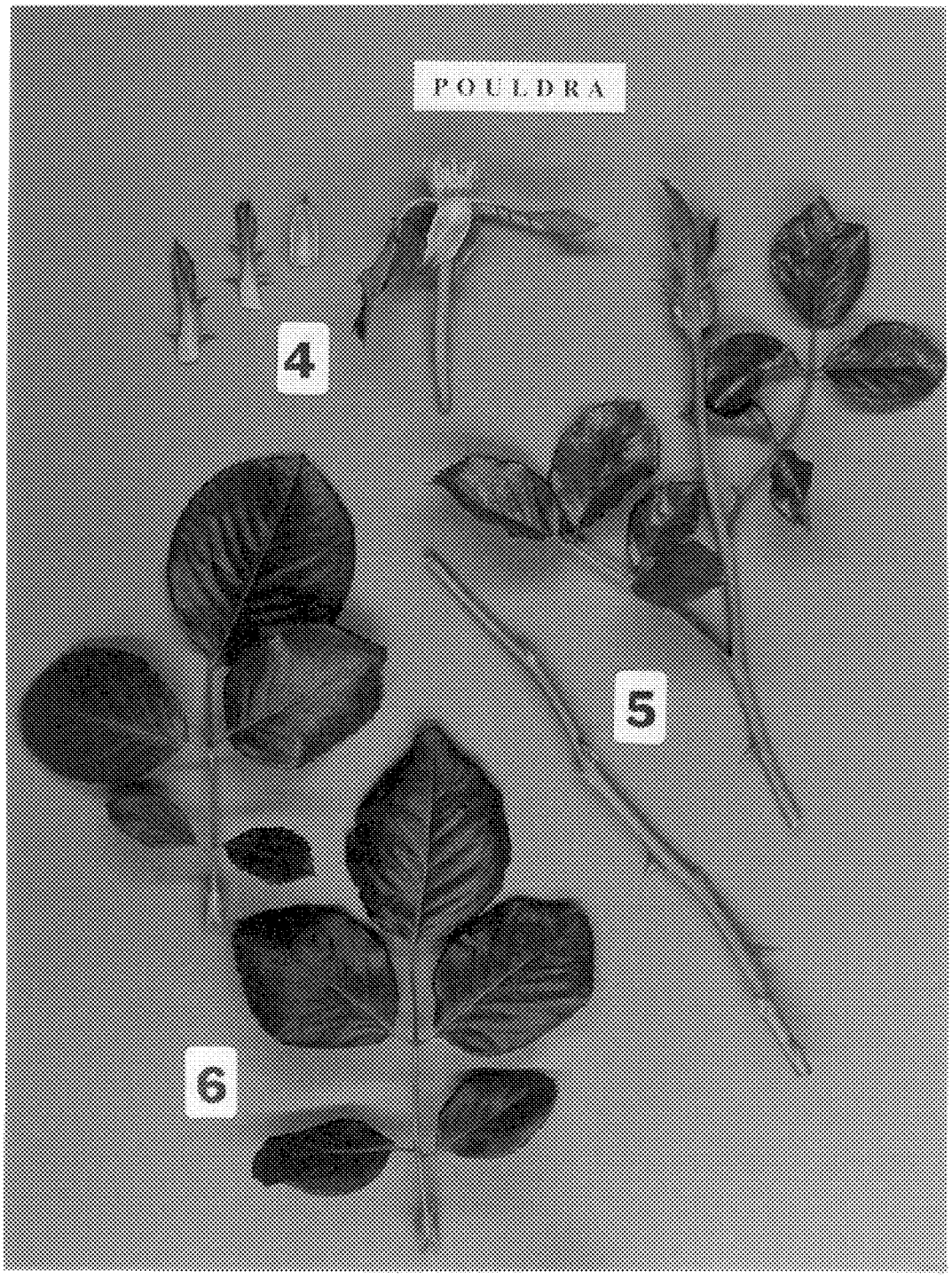
POULDRA
4
5
6